(12) United States Patent
Crnkovich et al.

(10) Patent No.: US 10,960,119 B2
(45) Date of Patent: Mar. 30, 2021

(54) METHOD FOR OPERATING A BLOOD TREATMENT APPARATUS, CONTROL UNIT AND TREATMENT APPARATUS FOR EXECUTING THE METHOD

(71) Applicants: Fresenius Medical Care Deutschland GmbH, Bad Homburg (DE); Fresenius Medical Care Holdings, Inc., Waltham, MA (US)

(72) Inventors: Martin Joseph Crnkovich, Walnut Creek, CA (US); Christian Schlaeper, Wehrheim (DE)

(73) Assignees: Fresenius Medical Care Deutschland GmbH, Bad Homburg (DE); Fresenius Medical Care Holdings, Inc., Waltham, MA (US)

( * ) Notice: Subject to any disclaimer, the term of this patent is extended or adjusted under 35 U.S.C. 154(b) by 808 days.

(21) Appl. No.: 15/585,498

(22) Filed: May 3, 2017

(65) Prior Publication Data
US 2018/0318486 A1 Nov. 8, 2018

(51) Int. Cl.
*A61M 1/16* (2006.01)
*A61M 1/34* (2006.01)
*A61M 1/36* (2006.01)
*G16H 40/63* (2018.01)
*G16H 20/17* (2018.01)
(Continued)

(52) U.S. Cl.
CPC .......... *A61M 1/1601* (2014.02); *A61M 1/34* (2013.01); *A61M 1/3612* (2014.02); *A61M 1/3621* (2013.01); *A61M 1/3646* (2014.02); *G16H 10/65* (2018.01); *G16H 20/17* (2018.01); *G16H 40/40* (2018.01); *G16H 40/63* (2018.01); *A61M 2230/207* (2013.01); *A61M 2240/00* (2013.01)

(58) Field of Classification Search
CPC .............. A61M 1/1601; A61M 1/3612; A61M 1/3646; A61M 1/34; A61M 1/3621; A61M 2230/207; A61M 2240/00; G16H 20/17; G16H 40/40; G16H 40/63; G16H 10/65
See application file for complete search history.

(56) References Cited

U.S. PATENT DOCUMENTS

| | | |
|---|---|---|
| 5,823,986 A | 10/1998 | Peterson |
| 6,387,323 B1 | 5/2002 | Afzal et al. |
| 6,533,747 B1 | 3/2003 | Polaschegg et al. |

(Continued)

FOREIGN PATENT DOCUMENTS

| | | |
|---|---|---|
| EP | 2253342 | 11/2010 |
| WO | WO 96/25214 | 8/1996 |

(Continued)

*Primary Examiner* — Philip R Wiest
(74) *Attorney, Agent, or Firm* — Fish & Richardson P.C.

(57) ABSTRACT

A method for operating a blood treatment apparatus including an extracorporeal blood circuit having a blood filter with a blood chamber and a dialysate chamber, between which a membrane is arranged. The method encompasses operating a blood pump from a first time point, at which an ultrafiltration pump is stopped, at least until a second time point, at which at least one of the following conditions is met for the first time after the first time point: a time interval after has elapsed, the blood pump has conveyed a volume after, a measurement of a fluid in the extracorporeal blood circuit exceeds or falls below a threshold.

18 Claims, 5 Drawing Sheets

(51) Int. Cl.
   *G16H 40/40*      (2018.01)
   *G16H 10/65*      (2018.01)

(56) References Cited

U.S. PATENT DOCUMENTS

| | | |
|---|---|---|
| 7,387,734 B2 | 6/2008 | Felding |
| 7,780,848 B2 | 8/2010 | Kim et al. |
| 7,785,463 B2 | 8/2010 | Bissler et al. |
| 8,409,441 B2 | 4/2013 | Wilt |
| 8,491,518 B2 | 7/2013 | Schnell et al. |
| 8,721,884 B2 | 5/2014 | Wilt et al. |
| 9,480,784 B2 | 11/2016 | Kelly et al. |
| 9,579,440 B2 | 2/2017 | Hogard et al. |
| 9,603,985 B2 | 3/2017 | Wilt et al. |
| 2010/0192686 A1* | 8/2010 | Kamen ............... A61M 1/3646 73/290 R |
| 2012/0323157 A1* | 12/2012 | O'Mahony ............. A61M 1/34 604/4.01 |
| 2013/0094996 A1 | 4/2013 | Janssenswillen |
| 2013/0199998 A1 | 8/2013 | Kelly et al. |

FOREIGN PATENT DOCUMENTS

| | | |
|---|---|---|
| WO | WO 2000/043055 | 7/2000 |
| WO | WO 2018/054901 | 3/2018 |

\* cited by examiner

METHOD FOR OPERATING A BLOOD TREATMENT APPARATUS, CONTROL UNIT AND TREATMENT APPARATUS FOR EXECUTING THE METHOD

TECHNICAL FIELD

The disclosure relates to a method for operating a blood treatment apparatus utilized for a blood treatment of a patient. It further relates to a control unit, to a medical treatment apparatus for executing the method, a digital storage medium, a computer program product as well as a computer program.

BACKGROUND

During or after the end of an extracorporeal blood treatment, the blood which is present in the extracorporeal circuit is usually displaced from the extracorporeal blood circuit in direction of the vascular system of the patient by means of a substitute liquid (hereafter also shortly referred to as substitute) and is thus reinfused into the patient. It is often desirable to reinfuse as much of the patient's blood from the blood treatment apparatus as is technically possible to minimize the loss of valuable blood cells and other blood constituents. However, a certain amount of substitute is infused into the patient when the blood is reinfused.

Since removing parts of the liquid fraction from the blood of the patient is usually a therapeutic target, the infusion of substitute is undesired and even counterproductive, as the preceding treatment was expressly intended, amongst others, to remove water from the patients' blood.

This is all the more relevant for pediatric patients, who may afford the loss of blood cells less than others and whose total blood value is smaller, such that the reinfusion of substitute may be more detrimental than for other patients.

SUMMARY

In an aspect of the disclosure, a method is proposed for operating a blood treatment apparatus, wherein the blood treatment apparatus includes a blood filter. The blood filter includes a blood chamber and a dialysate chamber, between which a membrane is arranged.

The blood chamber is connected for the purpose of blood treatment to an arterial section leading to the blood chamber and to a venous section leading away from the blood chamber.

The dialysate chamber is connected to a dialysis inlet line, which leads to the dialysate chamber and to a dialysate outlet line, which leads away from the dialysate chamber.

The method encompasses operating a blood pump from a time point $t_{UF\text{-}stop}$, at which an ultrafiltration pump is stopped, at least until a time point $t_{BP\text{-}min}$, at which at least one of the following conditions is met for the first time after $t_{UF\text{-}stop}$:

(a) a time interval $T_{post\text{-}UF\text{-}stop}$ (after $t_{UF\text{-}stop}$) has elapsed (b) the blood pump has conveyed a volume $V_{post\text{-}UF\text{-}stop}$ after $t_{UF\text{-}stop}$ (c) a measurement value of a fluid in the extracorporeal blood circuit exceeds or falls below a certain threshold.

The blood pump is thus operated at least from $t_{UF\text{-}stop}$ until $t_{BP\text{-}min}$. In some implementations the blood pump may be operated before $t_{UF\text{-}stop}$ and/or after $t_{BP\text{-}min}$.

In a further aspect of the disclosure, the control unit, which may also be designed as a regulating unit, is suitable and provided and/or programmed and/or arranged and/or configured for executing the method in interaction with a medical blood treatment apparatus. It can optionally include further devices such as, for example, storage devices, addition devices, (preferably automated) signal generating devices and so on.

In another aspect of the disclosure, the medical treatment apparatus (hereafter also in short: treatment apparatus) includes optionally at least one extracorporeal blood circuit having a conduit interior. It is further equipped with at least one blood pump for conveying blood within the conduit interior of the extracorporeal blood circuit, the blood pump being arranged or arrangeable in the extracorporeal blood circuit. In addition, it includes a control unit.

According to yet another aspect of the disclosure, a storage medium, in particular a digital one, in particular a non-volatile one, in particular a floppy disk, RAM, ROM, CD, hard disk, USB stick, flash card, SD card, or EPROM, in particular with electronically or optically readable control signals may interact with a programmable computer or computer system such that the machine-induced steps of method described herein are prompted.

Herein, a computer system preferably includes at least a processor, random access memory (RAM) and non-volatile data storage, such as read-only memory (ROM).

In this, all or some of the steps of the method which are executed by the machine may be prompted.

In another aspect of the disclosure, a computer program product includes a program code or machine control instructions saved on a volatile machine-readable storage medium for prompting the machine-induced steps of the method when the computer program product runs on a computer.

The term machine-readable storage medium, as used herein, denotes in certain implementations a medium which contains data or information which is interpretable by software and/or hardware. The medium may be a data medium such as a disk, a CD, DVD, a USB stick, a flashcard, an SD card an EPROM and the like.

In a further aspect of the disclosure, a computer program includes a program code for prompting the machine-induced steps of the method when the computer program runs on a computer.

In this, all, several or some of the steps of the method which are executed by the machine may be prompted.

A computer program product can be understood as, for example, a computer program which is stored on a data storage medium, a signal wave, an embedded system as a comprehensive system with a computer program (e.g. an electronic device with a computer program), a network of computer-implemented computer programs (e.g. a client-server system, a cloud computing system, etc.) or a computer on which a computer product is loaded, executed, saved or developed.

Herein, a computer program can be understood as, for example, a physical software product ready for distribution, which contains a computer program.

All or some of the steps of the method, which are executed by the machine, may be prompted by the computer program product and/or the computer program when it is running on a computer system.

In all of the implementations disclosed herein, the use of the expression "may be" or "may have" and so on, is to be understood synonymously with "preferably is" or "preferably has," and so on respectively, and is intended to illustrate an implementation.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" encompassing "at least one". This understanding is also equally encompassed by the present disclosure as the interpretation that a numerical word, for example, "one" may alternatively mean "exactly one", wherever this is evidently technically possible for the person skilled in the art. Both are encompassed by the present disclosure and apply herein to all used numerical words.

A blood mixture describes a mixture of blood and at least one further fluid, in particular one further liquid. A blood mixture is for example a mixture of blood and substitute, which is, e.g., a solution, such as, e.g., a fresh dialysis liquid, physiological saline solution etc.

A "substitute" may for example be any substitute or fresh dialysis liquid generally known for use in a blood treatment, e.g., hemodiafiltration. A substitute is preferably a solution, e.g., isotonic saline solution, e.g., a solution containing 0.9% NaCl, which may already be used during the blood treatment session and is thus a solution already introduced or introducible through a fluid communication into the extracorporeal blood circuit. The term "substitute" may also mean herein "exchange liquid".

Q describes a flow rate, herein also described in short as flow. $Q_{UF}$ describes the flow rate through an ultrafiltration pump (herein also in short: UF pump), $Q_{BP}$ describes the flow rate through a blood pump, $Q_{substutuate\_pump}$ describes the flow rate through by a substitute pump, $Q_{conveying\_device}$ describes the flow rate through a conveying device and $Q_{patient}$ describes the flow rate at which the patient is being reinfused with blood or blood mixture.

Advantageous implementations are each subject-matter of the dependent claims and implementations.

Implementations may include one or several of the following features in any combination, unless the person skilled in the art recognizes their combination as technically impossible.

In some exemplary implementations, the medical treatment apparatus includes a device, e.g. a conveying device, such as, e.g., a substitute pump, blood pump or fresh dialysis liquid pump, which is provided to introduce substitute into the extracorporeal blood circuit, e.g., into the arterial section. The conveying device, which is provided for introducing substitute, is referred to hereafter also as conveying device for substitute.

In some exemplary implementations, one or several of the following actuators or conveying devices are used for the method:

(i) A conveying device for substitute, in particular a substitute pump and/or a blood pump.
(ii) A filter which includes a semi-permeable membrane and connection on the side of the fresh dialysis liquid and/or a connection on the side of the device.
(iii) A pump, which builds a pressure, in particular a positive or negative pressure, which pressure drives a transmembrane flow from the blood side of the filter to the dialysate side of the filter. This pump is in some implementations identical to the pump that conveys substitute. In other implementations, the two mentioned pumps are not identical to each other, and are implemented separately. In some implementations the pump, which builds the pressure or negative pressure, is an ultrafiltration pump (short: UF pump). The UF pump preferably generates a negative pressure in the dialysate chamber.
(iv) A flow resistance. The flow resistance is preferably situated in the extracorporeal blood circuit on the outflow side of the blood chamber of the blood filter, such that a positive pressure (relative to the dialysate side of the filter) is created in the blood chamber due to the flow resistance in conjunction with the aforementioned pump, which builds up pressure.

In some implementations, the time interval $T_{post-UF-stop}$ of condition (a) in claim 1 is at least $T_{minimum}$. In some implementations $T_{minimum}$ is 1 min, 2 min or 5 min (example values for $T_{minimum}$).

In some implementations, $T_{minimum}$ is dependent on the volume of the extracorporeal blood circuit $V_{EBC}$ and/or on the flow rate of the blood pump $Q_{BP}$.

In some implementations, $T_{minimum}$ is the time the blood pump (at a specific speed, the current speed, a maximum speed or a minimum speed) needs to displace the entire blood in the extracorporeal blood circuit or the blood downstream of the blood filter. In some implementations, a safety margin of 10%, 15%, 20% or 25% is applied to the the time periods, i.e., $T_{minimum}$ is longer by the the percentages than calculated according to the time necessary to displace a certain fluid volume at a certain pumping speed.

In some implementations, the volume $V_{post-UF-stop}$ of condition (b) in claim 1 is at least $V_{minimum}$. In some implementations, $V_{minimum}$ is at least 50 ml, preferably at least 100 ml, preferably at least 120 ml. (example values for $V_{minimum}$).

In some implementations, $V_{minimum}$ is dependent on the volume of the extracorporeal blood circuit $V_{EBC}$. In some implementations, $V_{minimum}$ is the total volume of the extracorporeal blood circuit or the volume of the extracorporeal blood circuit downstream of the blood filter. In some implementations, a safety margin of 10%, 15%, 20% or 25% is applied to the the volumes.

In some implementations, $V_{EBC}$ may be a value measured by the medical treatment apparatus, it may have been entered into the the apparatus manually, it may have been read from a storage element on or in a disposable or it may have been recalled from a memory of the the apparatus according to the kind of disposable currently used in the the apparatus.

In some implementations, the method is carried out after the end of the blood treatment session. For example, in an implementation, the time point $t_{UF-stop}$, at which the ultrafiltration pump stops, may signify the completion of a blood treatment session. In other implementations, the time point $t_{BP-min}$ may signify the completion of a blood treatment session. In further implementations, the blood treatment session may be completed at a different time, e.g., it may only be completed when the patient is disconnected from the medical treatment apparatus.

In some implementations, the method may be carried out after a user terminates the blood treatment session manually. In other implementations, the method may be carried out after the blood treatment session stops due to a pre-determined criterion being met.

In some implementations, the method may be carried out during the blood treatment session, preferably at the end of a blood treatment session.

In some implementations, the ultrafiltration pump stops at the time point $t_{UF-stop}$ only after at least one of the following events has occurred:
an ultrafiltration goal has been met
a prescribed treatment time has been reached.

In some implementations, the method encompasses operating the blood pump after $t_{UF-stop}$ at least until condition (c) of claim 1 has been met while condition (a) and/or (b) also have to be met. In this implementation, it is ensured that condition (c) of claim 1, namely that a measurement value of a fluid in the extracorporeal blood circuit exceeds or falls below a certain threshold, has been met before the blood pump may stop. At the same time, the minimum time duration $T_{post-UF-stop}$ and/or the minimum Volume $V_{post-UF-stop}$ requirement must also be achieved or reached before the blood pump may stop.

In some implementations of the method, the ultrafiltration pump is reactivated or restarted at $t_{BP-min}$ or thereafter. The reactivation of the ultrafiltration pump may further reduce the blood volume to be reinfused at the end or after the end of the blood treatment by the filtration of additional water. The delay in reactivation of the ultrafiltration pump may in some cases lead to the blood in the extracorporeal blood circuit to be replaced with fresh blood from the patient, thereby in some cases decreasing the hematocrit and/or Hb concentration in the extracorporeal blood circuit.

In some implementations of the method, the fluid content of the extracorporeal blood circuit is returned to the patient by introducing a substitute into the arterial section starting at $t_{BP-min}$ or thereafter.

Preferably, at least one of the ratios $Q_{UF}/Q_{BP}$ and $Q_{UF}/Q_{substutuate\_pump}$ increases while a substitute is introduced into the arterial section. Preferably, at least one of the ratios $Q_{UF}/Q_{BP}$ and $Q_{UF}/Q_{substutuate\_pump}$ is varied while a substitute is introduced into the arterial section in order to regulate the hematocrit (HKT) in the venous section towards a pre-determined value.

In some implementations, after $t_{UF-stop}$, at least one of the following is operated: the ultrafiltration pump, the blood pump, and the substitute pump, for at least some of the time period, during which the fluid content of the extracorporeal blood circuit is returned to the patient. Preferably, the ultrafiltration pump is operated again after it was stopped at time point $t_{UF-stop}$ and preferably only at $t_{BP-min}$ or thereafter. The interval during which the ultrafiltration pump is not operated after $t_{UF-stop}$ may allow for fresh blood from the patient to replace the highly concentrated blood in the extracorporeal blood circuit downstream of the blood filter.

In some implementations, during return of the fluid content of the extracorporeal blood circuit to the patient, the ultrafiltration pump is operated, after it was stopped at time point $t_{UF-stop}$ and after it was reactivated no earlier than $t_{BP-min}$, at least until at least one of the following conditions is met:
 (d) a measurement value of the fluid in the extracorporeal blood circuit exceeds or falls below a certain threshold;
 (e) the rinsing fluid volume introduced into the arterial section exceeds a certain value; and
 (f) a detected pressure exceeds a certain value.

In some implementations, when at least one of the conditions (d), (e) and (f) is met, the ultrafiltration pump is stopped.

In some implementations of the method, the substitute is introduced into the arterial section by the blood pump. In some of these implementations and after the ultrafiltration pump has stopped due to at least one of the conditions (d), (e) and (f) having been met, the blood pump continues running until at least one of the following conditions is met:
 (g) a measurement value recorded in the venous line exceeds or falls below a certain threshold
 (h) the rinsing fluid volume introduced into the arterial section exceeds a certain volume.

A measurement value, such as the measurement value according to condition (d) or (g), may be, e.g., a hematocrit, an optical density or an electromagnetic property, such as resistance or impedance. The measurement values considered for condition (d) and (g) may be based on the same measured parameter, alternatively, they are based on different measurement parameters.

In some implementations, a hematocrit is the measurement value of condition (d) and the ultrafiltration pump is stopped when the hematocrit exceeds a certain threshold. In this, the threshold for the hematocrit may be 30%, preferably 35%, preferably 40% or 45%.

The certain volume, which the rinsing fluid volume may exceed according to condition (h), may in some implementations be dependent on the extracorporeal blood volume. In some implementations the certain volume may be $V_{EBC}$ or $V_{EBC}$ plus the ultrafiltration volume since the start of blood return.

In some implementations, after $t_{UF-stop}$ and after $t_{BP-min}$, the ultrafiltration pump is reactivated, wherein a target rate of the ultrafiltration pump is calculated based on a flow rate, a measured value of the fluid in the extracorporeal blood circuit and/or on the water available in the extracorporeal blood circuit. The flow rate may be a blood flow rate in the extracorporeal blood circuit, in particular the flow rate through the blood pump $Q_{BP}$. The measured value of the fluid may be, e.g., a hematocrit or an optical density.

In some implementations after $t_{BP-min}$, the ultrafiltration rate depends on the blood flow rate and the hematocrit, e.g., a measured hematocrit or a default hematocrit. Such a default hematocrit may in some implementations be edited by the user. In some implementations, the value for the default hematocrit is 30%, 35%, 40% or 45%. The default hematocrit may in some implementations be between 30% and 45%, preferably between 35% and 40%.

In some implementations, the ultrafiltration rate after $t_{BP-min}$ is calculated according to:

$$Q_{UF} = Q_{BP} \times cf\_UF$$

wherein $Q_{UF}$ is the ultrafiltration rate, $Q_{BP}$ is the flow rate through the blood pump and cf_UF is an ultrafiltration correction factor. The value cf_UF is an estimation of the fraction of the water content in the extracorporeal blood circuit, which may be safely removed by ultrafiltration. The factor cf_UF may in some implementations be between 10% and 50%, preferably between 15% and 40%, more preferably between 20% and 30%. In some implementations cf_UF may be determined by the user, it may be a default value or it may be calculated depending on the initial hematocrit and/or an upper limit or target hematocrit.

In some implementations, a target ultrafiltration rate may be calculated depending on the hematocrit at $t_{UF-stop}$ and a defined hematocrit limit as well as a flow rate in the extracorporeal blood circuit, e.g., $Q_{BP}$.

For at least some of the time period, during which substitute is introduced into the extracorporeal blood circuit and the fluid content of the extracorporeal blood circuit is returned to the patient, a pressure difference is generated in the blood filter with a lower pressure in the dialysate chamber and a higher pressure in the blood chamber, wherein the pressure difference is, at least partially, generated by at least one pump of the following pumps:
 the ultrafiltration pump
 the substitute pump
 the blood pump.

In the time, during which substitute is introduced into the extracorporeal blood circuit and the fluid content of the extracorporeal blood circuit is returned to the patient and a pressure difference is generated in the blood filter with a lower pressure in the dialysate chamber and a higher pressure in the blood chamber, at least one of the following flow rates is between 30 and 280 ml/min:

the flow rate ($Q_{BP}$) of the blood pump the flow rate ($Q_{substutuate\_pump}$) of the substituate pump.

In the time, during which substituate is introduced into the extracorporeal blood circuit and the fluid content of the extracorporeal blood circuit is returned to the patient and a pressure difference is generated in the blood filter with a lower pressure in the dialysate chamber and a higher pressure in the blood chamber, at least one of the following ratios is in a value range of 0.01 to 0.8:

the flow rate ratio ($Q_{UF}/Q_{BP}$) of the flow in the ultrafiltration pump to the flow in the blood pump the flow rate ratio ($Q_{UF}/Q_{substutuate\_pump}$) of the flow in the ultrafiltration pump to the flow in the substituate pump.

In applying the method, the UF pump and/or the flow resistance, in some implementations, cause a pressure difference between the blood side of the filter and the spent dialysate side of the filter, which results in a transmembrane flow from the blood side of the filter to the dialysate side of the filter. In this, preferably water and possibly low molecular components are pressed or drawn from the blood side to the dialysate side while cellular components remain on the blood side such that the hematocrit on the blood side may increase.

The blood return begins in some implementations—preferably immediately—after the completion of the actual therapy. The patient's blood is then, preferably according to a doctor's prescription, treated and the amount of water (or plasma) present in the patient's blood is reduced correspondingly, e.g. according to the prescription. In this, the therapy takes usually 3 to 5 hours. The duration may be set in advance. The termination of this period of time may indicate the completion of the blood treatment.

When the blood return ends, the device signals this to the operator in some implementations. This may be for example the case when the hematocrit present in the extracorporeal blood circuit is reduced (e.g. at a detection device, in particular at a venous substituate/blood detector) to a predetermined value (e.g. down to 2%).

In some implementations, the end of the blood treatment is displayed or communicated to the operator.

In some implementations, the method follows the termination of the blood treatment. In other implementations, the method is part of the blood treatment and is preferably carried out as a last step of the blood treatment.

The communication of the end of the blood treatment may be communicated to the operator e.g. by a display and/or per alarm.

The end of the blood treatment may be reached and/or displayed or communicated, when, e.g., the ultrafiltration volume being prescribed or set in advance is removed.

The end of the blood treatment may be reached and/or displayed or communicated, when the end of the treatment is communicated to the operator by means of the user interface.

The end of the blood treatment may be reached and/or displayed or communicated, when alarm systems or alarm limits, which are active during the blood treatment, have been deactivated.

In some implementations, at $t_{BP-min}$ or thereafter, no more blood is withdrawn from the patient The method begins preferably after the end of the blood treatment, preferably after a delay or immediately after its end.

In some implementations, the blood pump runs backwards during the execution of method.

"Backwards" may mean that the blood pump conveys in a direction towards the arterial patient connection or towards the arterial patient tube hose.

"Backwards" may mean that the blood pump conveys in a direction, which is opposite to the conveying direction of the blood pump during the blood treatment.

In some implementations, the blood pump conveys substituate, which has been connected to the extracorporeal blood circuit for the purpose of blood reinfusion.

In some implementations, the blood pump conveys saline solution which is fed into the extracorporeal blood circuit from a bag or another container.

In some implementations, the arterial patient line and the venous patient line are connected to each other.

In some implementations, the arterial patient line and/or the venous patient line are connected, respectively, to a venous section or to an arterial section of the extracorporeal blood circuits or of a blood cassette.

In several exemplary implementations, the pressure difference between the blood chamber and the dialysate chamber of the blood filter is at least partially generated by at least one pump, in particular at least one of: a conveying device for substituate, an ultrafiltration pump, a substituate pump and a blood pump. Preferably, this is the case while the fluid content of the extracorporeal blood circuit is returned to the patient by introducing a substituate into the extracorporeal blood circuit at $t_{BP-min}$ or thereafter.

In the method, the ultrafiltration pump runs in some implementations at least temporarily concurrently with at least one of: the conveying device for substituate, the substituate pump and the blood pump. Preferably, this occurs while a substituate is introduced into the extracorporeal blood circuit. In this way, a pressure difference between the blood chamber and the dialysate chamber of the blood filter may be generated in some implementations.

In certain implementations, the conveying device for substituate, in particular at least one of the blood pump and the substituate pump, conveys at a flow rate $Q_{conveying\_device}$, $Q_{BP}$ or $Q_{substutuate\_pump}$ of between 20 and 300 ml/min, preferably between 30 and 280, between 70 and 240, and particularly preferably between 150 and 210 ml/min. Preferably, the conveying device for substituate conveys at these rates while substituate is introduced into the extracorporeal blood circuit.

In some implementations, preferably while substituate is introduced into the extracorporeal blood circuit, the ultrafiltration pump conveys preferably at a fraction of the flow rate of the conveying device for substituate, in particular at least one of the blood pump and the substituate pump conveys, such that the ratio $Q_{UF}/Q_{conveying\_device}$, $Q_{UF}/Q_{BP}$ or $Q_{UF}/Q_{substutuate\_pump}$ is preferably in a value range between 0.005 to 0.9 or between 0.01 to 0.8, particularly preferably, between 0.1 to 0.7 and most preferably between 0.2 to 0.6. In this, $Q_{UF}$ is preferably between 1 and 80 ml/min.

In some implementations of the method, preferably while substituate is introduced into the extracorporeal blood circuit, the ultrafiltration pump conveys preferably between 1 ml/min and 150 ml/min, particularly preferably between 15 ml/min and 150 ml/min.

In some implementations of the method, preferably while substituate is introduced into the extracorporeal blood circuit, the ultrafiltration pump conveys preferably between 15 ml/min and 150 ml/min, particularly preferably between 20 ml/min and 150 ml/min.

In some implementations of the method, preferably while substitute is introduced into the extracorporeal blood circuit, the ultrafiltration pump conveys preferably at above 15 ml/min, particularly preferably at above 20 ml/min. This may advantageously accelerate the reinfusion. In addition, the mixing of substitute and blood may in this way be advantageously limited to a short or shorter length of tubing when compared to the prior art.

In some implementations of the method, the conveying rates given herein are at least temporarily reached.

In some implementations, the flow rate or the quotient $Q_{conveying\_device}$, $Q_{UF}$ and/or $Q_{BP}$ is automatically controlled or regulated by the device, preferably while substitute is introduced into the extracorporeal blood circuit.

In some implementations and at the beginning of the return of blood from the extracorporeal blood circuit while infusing substitute into the extracorporeal blood circuit, $Q_{UF}/Q_{conveying\_device}$, $Q_{UF}/Q_{BP}$ or $Q_{UF}/Q_{substituate\_pump}$ is set low or lower than at a later time, since the hematocrit of the liquid in the filter is usually still high and a comparatively strong increase in viscosity or hematocrit should be avoided. In further course, the quotient is preferably increased, since the hematocrit of the liquid in the filter has typically decreased in the meantime. The hematocrit of blood/substitute mixture is preferably increased through the method, such that the patient is advantageously infused with as little substitute as possible.

In some implementations, $Q_{UF}/Q_{conveying\_device}$, $Q_{UF}/Q_{BP}$ and/or $Q_{UF}/Q_{substutuate\_pump}$ increases with increasing infused volume of substituate, preferably infused into the extracorporeal blood circuit. The increase occurs preferably monotonically, particularly preferably strictly monotonically. The following table, Table 1, indicates for an implementation the exemplary connection between $Q_{UF}/Q_{BP}$ for a volume of the extracorporeal circuit of about 200 ml.

TABLE 1

| Introduced substituate volume into the extracorporeal blood circuit $V_{substituate}$ [ml], cumulative | $Q_{UF}/Q_{BP}$ |
|---|---|
| 0 | e.g. 0.1; typically: 0.01 to 0.3 |
| 40 | e.g. 0.1; typically: 0.01 to 0.3 |
| 80 | e.g. 0.3; typically: 0.1 to 0.5 |
| 120 | e.g. 0.5; typically: 0.1 to 0.7 |
| 160 | e.g. 0.6; typically: 0.3 to 0.8 |
| 200 | e.g. 0.7; typically: 0.5 to 0.8 |
| 240 | e.g. 0.7; typically: 0.5 to 0.8 |
| 280 | e.g. 0.7; typically: 0.5 to 0.8 |

In an implementation, the desired flow rate of the substituate, in particular the flow rate into the extracorporeal blood circuit, is adjustable by the operator. The flow to the patient ($Q_{patient}$) is preferably set according to the following rule: $Q_{patient} = Q_{conveying\_device} - Q_{UF}$, in particular $Q_{patient} = Q_{BP} - Q_{UF}$, wherein the blood pump is in this example the sole conveying pump for substituate.

In some implementations, the desired flow into the patient ($Q_{PatientDesired}$), in particular when introducing substituate into the arterial section, is adjustable by the operator and the device calculates, e.g., recurringly or continuously, $Q_{conveying\_device}$ or $Q_{BP}$ according to the rule:

$$Q_{conveying\_device} = Q_{PatientDesired} + Q_{UF},$$

in particular $Q_{BP} = Q_{PatientDesired} + Q_{UF}$.

In some implementations, $Q_{UF}/Q_{conveying\_device}$, $Q_{UF}/Q_{BP}$ and/or $Q_{UF}/Q_{substutuate\_pump}$ is controlled (e.g., in the sense of a rising ramp) depending on the amount of substituate conveyed so far.

In some implementations of the method, $Q_{UF}/Q_{conveying\_device}$, $Q_{UF}/Q_{BP}$ and/or $Q_{UF}/Q_{substutuate\_pump}$ is controlled (e.g., rising ramp) depending on the amount of the substituate already conveyed and on the volume of the extracorporeal blood circuit known e.g. from the filling of the system. For example, $Q_{UF}/Q_{conveying\_device}$ of the conveyed substituate increases monotonically, preferably strictly monotonically. $Q_{UF}/Q_{conveying\_device}$ is, particularly preferably, proportional to the already-conveyed substituate volume.

In some implementations of the method, $Q_{UF}/Q_{conveying\_device}$, $Q_{UF}/Q_{BP}$ and/or $Q_{UF}/Q_{substutuate\_pump}$ is individually controlled depending on a prescription or on acute requirements of the patient.

In some implementations, the $Q_{UF}/Q_{conveying\_device}$, $Q_{UF}/Q_{BP}$ and/or $Q_{UF}/Q_{substutuate\_pump}$ is varied during the execution of the method, preferably while substituate is introduced into the extracorporeal blood circuit, e.g., in order to regulate the hematocrit, e.g., in the venous section to a pre-determined value.

In some implementations, $Q_{UF}/Q_{conveying\_device}$, $Q_{UF}/Q_{BP}$ and/or $Q_{UF}/Q_{substutuate\_pump}$ is varied in order to regulate the hematocrit in the extracorporeal blood circuit to a desired value (typically between 30 and 60%), preferably while substituate is introduced into the extracorporeal blood circuit. For example, the flow pressure of the filter on the blood side may be used as the input value of the regulator (e.g. $P_{filter\_longitudinal}$ = pre-filter (post pump)pressure – post-filter (venous)pressure, i.e. the pressure which is present between pump and filter inlet, minus the pressure which is present in the venous line downstream of the filter). In this, the flow resistance is proportional to the viscosity of the liquid in the extracorporeal blood circuit. The viscosity is proportional to the hematocrit of the blood in the filter.

In some implementations, while introducing substituate into the extracorporeal blood circuit, $Q_{UF}/Q_{conveying\_device}$, $Q_{UF}/Q_{BP}$ and/or $Q_{UF}/Q_{substutuate\_pump}$ is regulated depending on the hematocrit, for example in the venous section, wherein the hematocrit is determined by means of the detection device, in particular by means of the venous substituate/blood detector, and depending on a pre-determined substituate volume to be saved. For example, the operator specifies an amount of substituate to be saved (as compared to blood return without ultrafiltration) and $Q_{UF}/Q_{conveying\_device}$, $Q_{UF}/Q_{BP}$ and/or $Q_{UF}/Q_{substutuate\_pump}$ is varied or regulated depending on the hematocrit of the liquid, e.g., in the venous patient line (e.g., detected by an optical detector, e.g., a venous substituate/blood detector).

In some implementations, $Q_{UF}/Q_{conveying\_device}$, $Q_{UF}/Q_{BP}$ and/or $Q_{UF}/Q_{substutuate\_pump}$ is set, in the case of simultaneous arterial and venous reinfusion, depending on the hematocrit of the liquid in the arterial patient line such that the hematocrit of the liquid, which flows through the venous patient line into the patient, is relatively high (e.g., >50%, preferably >55%, particularly preferably about 60%). For example, the liquid from the arterial patient line having a comparatively low hematocrit (e.g. 10%) may mix, when reinfused into the patient's vascular system, with the liquid from the venous patient line having a high hematocrit (e.g. 60%), such that a hematocrit results in the patient's vascular system with a value (e.g. <60%), which lies between the values for the hematocrit in the venous or the arterial patient line. In this way, a particularly low reinfusion of substrate may be advantageously achieved in some implementations.

In some implementations of the method, $Q_{UF}/Q_{conveying\_device}$, $Q_{UF}/Q_{BP}$ and/or $Q_{UF}/Q_{substutuate\_pump}$ is set such that together with the amount of water, which is removed from the blood already prior to the blood return, the value of the prescription results.

In some implementations, the method may advantageously be used in any known reinfusion method (e.g. NaCl, online, online simultaneously etc.).

In some implementations, the method serves to partially, in others to completely, remove blood from a blood filter and/or blood circuit used for the blood treatment of a patient, preferably after completion of the blood treatment session and/or after $t_{UF\text{-}stop}$ and/or $t_{BP\text{-}min}$.

The utilized blood filter is in some implementations a hemodialyzer or a hemofilter.

The membrane arranged between the blood chamber and the dialysate chamber is in certain implementations a semipermeable membrane.

In specific implementations, the venous section leads from the blood chamber of the blood filter to a venous section (herein also denoted as venous air separation chamber) and/or a venous connection point or connection device.

In certain exemplary implementations, the arterial section leads from an arterial connection point or connection device to the blood chamber of the blood filter.

In specific exemplary implementations, the medical treatment apparatus and/or the blood filter is connected to a blood cassette.

In some implementations of the method, the method encompasses detecting a qualitative change of the content of the conduit interior of the extracorporeal blood circuit.

In some implementations of the method, a pre-determined amount of substituate is introduced into the conduit interior of the extracorporeal blood circuit by operating a conveying device, for example the blood pump, the substituate pump or the fresh dialysis liquid pump.

In some particular implementations, a substituate (alternatively denoted as substituate liquid) or fresh dialysis liquid is conveyed until the detection device detects a substituate, by a measurement value exceeding or falling below a pre-determined threshold, in the conduit interior of the extracorporeal blood circuit.

In some implementations of the method, the detection device is arranged at a pre-determined distance to a venous access device. In these implementations, the method may further encompass conveying the content of the conduit interior of the extracorporeal blood circuit across the pre-determined distance to the venous access device after dialysate has been detected at or by the detection device.

In certain implementations, blood contained in the conduit interior of the extracorporeal blood circuit is introduced into the vascular system of the patient via the venous access device.

In some implementations, the method further encompasses introducing air into the extracorporeal blood circuit, for example after completion of a blood treatment session and/or after the partial or complete removal of blood from the extracorporeal blood circuit.

A "blood treatment session" may be, for example, a treatment unit comprising hemodialysis, hemofiltration, hemodiafiltration and/or a cell separation method and it is directed to the treatment and/or purification of blood. For performing such a blood treatment, a suitable blood treatment apparatus is used.

A blood treatment apparatus which is suitable for executing the method includes, or is connected to, in some implementations an extracorporeal blood circuit having a conduit interior, at least one conveying device for introducing and/or conveying at least two fluids in the conduit interior of the extracorporeal blood circuit, and for example a device for treating the blood of the patient, such as one or several blood filters and/or one or several dialyzers and/or one or several adsorbents. It may further include containers for storing fluids, elements for introducing the fluids, such as for example tube elements and/or valves, as well as further devices, such as for example an air separation chamber or bubble trap for removing air from the blood during the blood treatment and/or sensors and/or detectors for detecting various relevant parameters, such as for example a pressure in the extracorporeal blood circuit.

Conveying devices, as mentioned herein, include membrane pumps, tube pumps and roller pumps etc. The blood pump, a substituate pump and/or a fresh dialysis liquid pump may be implemented, e.g., as a tube pump or a roller pump. However, also a different type of pump may be used, e.g., a membrane pump.

A conveying device for fresh dialysis liquid or substituate may be a "second" conveying device, i.e., a conveying device which is not identical to the blood pump. The blood pump may, however, also be designed such that it both executes the function which is typical for a blood pump as well as is able to perform the function of introducing substituate into the conduit interior and/or conveying the conduit content. Whenever a conveying device for substituate is mentioned herein, this relates, just for the purpose of better readability, to the blood pump or to a different conveying device. Both alternatives are equally encompassed by the present disclosure.

The method encompasses in certain implementations the step of introducing air into the conduit interior of the extracorporeal blood circuit for emptying it from fluid, e.g., by operating the blood pump. The air may for example be atmospheric air. The method is, however, not intended to be limited to the sole use of air, rather to include all gaseous fluids in addition to air which are suitable for the purposes of the present method.

"Introducing air into the conduit interior of the extracorporeal blood circuit" after completing the blood treatment session may occur exclusively by or may be supported by means of the blood pump, by means of the second conveying device or by means of a compressed air source.

Combinations of the aforementioned options are also encompassed by the present method, as well as a passive admission of air.

"Introducing substituate into the conduit interior of the extracorporeal blood circuit" takes place, as described above, in some particular implementations by operating the conveying device for substituate, in particular at least one of the blood pump and the substituate pump.

The blood pump may convey substituate by drawing it from a supply line to a container for the substituate, wherein the supply line enters into the extracorporeal blood circuit upstream of the suction side of the blood pump. For this, e.g., an outlet with a tube clamp which is provided in the arterial branch of the extracorporeal blood circuit may be provided.

A further implementation encompasses detecting a qualitative change of the content of the conduit interior of the extracorporeal blood circuit by means of at least one detection device, which is arranged in or at a section of the extracorporeal blood circuit.

The "qualitative change" may relate to one or several areas or sections of the extracorporeal blood circuit, for example an area or section in which the detection device is arranged.

"A qualitative change of the content of the conduit interior" includes a change in the composition of the content of the conduit interior, such as for example a change of the individual parts of blood and/or substitute in the conduit interior or a section thereof, in relation to each other. Also the lack of a fluid, which was previously present, may represent a change in the composition. A qualitative change may also be a transition from blood to substitute. Such changes may for example be easily detected, because of an optical change of the content, such as darkening change in the optical density of the content or a color change, e.g., a change from a red to a colorless, transparent fluid.

The "detection device" which is arranged in a section of the extracorporeal blood circuit may for example be an optical sensor which detects an optical change of the content of the conduit interior or another property of its content. Further suitable sensors include pressure sensors, conductivity sensors and sensors for detecting a change in the density of the content of the conduit interior of the extracorporeal blood circuit, without being limited thereto. In some implementations, a detection device is, or includes, a substitute/blood detector.

The "section of the extracorporeal blood circuit" may be an arterial and/or venous section of the extracorporeal blood circuit. The "arterial section" relates to a section of the extracorporeal blood circuit through which blood flows from the vascular system of the patient in the direction towards the blood treatment apparatus and/or towards the blood filter. The "venous section" refers to the section of the extracorporeal blood circuit through which the blood from the blood treatment apparatus and/or from the blood filter flows back to the vascular system of the patient.

In another implementation, the extracorporeal blood circuit encompasses at least one access device, which is connectable to a section of the vascular system of the patient, and the method encompasses disconnecting the extracorporeal blood circuit from the vascular system of the patient, in particular in the area of a first, for example arterial, access device, in particular at an end of the extracorporeal blood circuit.

"Disconnecting the extracorporeal blood circuit from the vascular system of the patient" means interrupting a connection between the extracorporeal blood circuit and the vascular system of the patient in a section of the extracorporeal blood circuit, for example at an end thereof. In doing so, the interruption may take place both at the arterial and at the venous section, wherein in some implementations, disconnecting the arterial section of the extracorporeal blood circuit is preferred.

Disconnecting in the "area of the first access device" may be understood as for example pulling out the arterial connection needle of a double-needle access.

Disconnecting may also be understood as interrupting the flow connection between the arterial section of the extracorporeal blood circuit and the arterial connection needle.

In the case of the single-needle version, disconnecting may be understood as interrupting the connection between the arterial leg of the "Y"-shaped section of the extracorporeal blood circuit and the only connection needle which is connected to the vascular system of the patient. The open lumen of the arterial leg of the Y-part may be closed in any manner (manually, machine-induced, automatically etc.) after being separated.

Alternatively, or in addition, the same may be also applied to the venous section of the extracorporeal blood circuit and the venous access to the vascular system of the patient.

An "addition point for the extracorporeal blood circuit for substituate into the conduit interior of the extracorporeal blood circuit" may be arranged in the arterial and/or the venous section of the extracorporeal blood circuit. It is preferred that the "addition point" is arranged in a section of the extracorporeal blood circuit, which is perfused upstream of the blood treatment apparatus, as well as for example upstream of the blood filter.

Suitable examples for an addition point include an opening/closing valve, a stop cock, a connectable branch line of a branched section of the extracorporeal blood circuit etc.

A "pre-determined substitute amount or fresh dialysis liquid amount" may correspond to a certain feed volume and/or a certain path length of the conduit interior of the extracorporeal blood circuit along which path the content is conveyed and can, for example, be produced by operating a membrane pump.

The substitute amount or the fresh dialysis liquid amount may preferably be pre-determined as a parameter, for example as a volume with a preset value and unit. The absolute amount of the substitute may preferably be stored and/or may be entered for example in a control unit of the treatment apparatus. The substitute amount may preferably be conveyed precisely, as far as the technical limits of precision permit.

In order to pre-determine an exact amount of substitute, e.g., technical specifications of the utilized extracorporeal blood circuit, such as for example the inner volumes of the tube set, may be stored in or entered into the control unit. By means of the technical specifications of the individual components of the extracorporeal blood circuit, for example a required feed time and/or a feed volume may be calculated.

A "limited amount of substitute or fresh dialysis liquid" may be for example an amount of substitute liquid which was chosen according to the operating personnel's empirical values. Preferably, a limited amount of fluid may be introduced and conveyed for so long until substitute is detected in the conduit interior of the extracorporeal blood circuit at a further detection device. A limited substitute amount thus does not have to be exactly known and/or to correspond to a certain feed volume. A limited amount of substitute may, however, be indirectly limited by the inner volume of the components of the extracorporeal blood circuit through which the substitute amount flows, in particular the inner volume of the section between the addition point for substituate and/or the blood treatment apparatus and a further detection device. In this way, the volume is thus determined in the sense of being "limited", however, without being exactly known, and without being expressible for example in milliliters and/or without having been stored or being enterable in a controller. Introducing a limited amount of substitute may be of advantage, e.g., if the type of the filter of a blood treatment apparatus or its capacity is unknown or incorrectly stated.

In doing so, the substitute may be introduced from a provided storage container into the extracorporeal blood circuit at the addition point for the substitute via corresponding conduit systems of the extracorporeal blood circuit.

The "detection device" is defined as above and may be arranged for example in the venous section of the extracorporeal blood circuit, e.g., between the blood treatment apparatus and the venous access device to the vascular system of the patient and in particular between a drip chamber in the venous section and the venous access device.

The detection device may detect the occurrence of substituate in a certain section of the conduit interior of the extracorporeal blood circuit, for example by means of an optical change of the content of the line interior.

If the detection device detects the presence of air or substituate in the conduit interior of the extracorporeal blood circuit, conveying the "substituate/blood content" may be stopped.

This may take place by stopping the respective conveying device.

Further, in another implementation of the method, it is preferred to arrange the detection device with a predefined distance to a second access device and to convey the content of the conduit interior along the predefined distance to the access device after substituate or a pre-determined transmission or light transmission, a pre-determined color or a pre-determined change of color has been recognized at the detection device.

In a further implementation of the method, the blood contained in the conduit interior of the extracorporeal blood circuit is returned into the vascular system of the patient—in particular substantially completely—via the second access device. The term "substantially completely returned" means herein that the blood present in the conduit interior of the extracorporeal blood circuit is removed nearly without any remaining substance from the extracorporeal blood circuit. The blood residues possibly remaining in the extracorporeal blood circuit for technical reasons, such as wetting behavior, or the blood residues remaining in the drip chamber are herein to be regarded as negligibly small.

"Returning blood into the vascular system of the patient" may take place if or when an end of the extracorporeal blood circuit, such as for example the end of the venous section, e.g., the venous connection needle, is connected to the vascular system of the patient. This connection may be maintained or re-established after the completion of the blood treatment session.

Due to the fact that the method as described herein is executable with the treatment apparatus, for the description of the blood treatment apparatus, it is referred to the respective implementations of the method, as described herein and vice versa, in order to avoid repetition.

An implementation of the treatment apparatus provides the arrangement of at least one detection device for detecting at least one change of the content of the conduit interior of the extracorporeal blood circuit or one property of the content in a section of the extracorporeal blood circuit. A property of the content may be a composition, a physical, chemical or biological parameter, for example an optical density, a pH value and much more suchlike. Such a detection device may correspond to the one described above, thus it is referred to its above description in order to avoid repetition.

A treatment apparatus may in some implementations, without being limited thereto, be suitable and/or configured to perform hemodialysis, hemofiltration, hemodiafiltration and/or separation methods.

One or more of the herein-mentioned advantages may be achievable via some implementations.

In some implementations, the method is changed or modified as compared to the prior art so that during the reinfusion procedure through the filter, water is removed from blood/blood mixture that resulted from displacing the blood by substituate. Due to this, in some implementations, the blood/substituate mixture, which leaves the filter towards the patient, contains in less substituate.

The net water which is removed in the entire treatment (including reinfusion) is usually an important treatment parameter for a patient with renal insufficiency. In order to remove a certain net amount of water from the patient's blood throughout the entire treatment, the water, which in addition to blood, has also necessarily been infused during the reinfusion, is usually already removed from the patient's blood in the course of the treatment before.

As the amount of water, which is removed in the actual treatment from the patient's blood, increases, the strain on the circulation of the patient often increases considerably. This often leads to physiological problems during the treatment. The amount of liquid, which is infused during the reinfusion and which—as described above—has been removed prior to completing the treatment, often leads to physiological problems as well. In some implementations, such physiological problems may be advantageously prevented or diminished.

The method may entail in some implementations one, several or all of the aforementioned or following advantages:

Reduced portion of substituate in the blood/substituate mixture, which is infused into the patient during the reinfusion. In this, the amount of water to be removed during the treatment preceding the method may be reduced.

Reduced reinfused blood (mixture) volume at the end/after the end of a blood treatment.

Improved circulation stability of the patient (in particular for pediatric patients).

Reduced amount of the vascular total liquid intake during the reinfusion.

Reduced duration of the reinfusion procedure.

Cost savings.

Reduced blood loss by the patient through less residual blood, which in the prior art remains in the extracorporeal blood circuit after the reinfusion. In the prior art, it is often a question whether the blood return should be accomplished as completely as possible, whereby a lot of substituate is infused, or whether as little as possible substituate should be infused, which is associated with a less efficient blood return and thus with a blood loss of the patient. The method avoids these disadvantages in some implementations.

Reduced anemia in dialysis patients.

Reduced need for drugs that aid blood formation (e.g. erythropoietin).

Increasing the patient's wellbeing.

Reduction of the effective treatment time (dialysis) during the reinfusion and corresponding reduction of the dialysis time (with corresponding cost saving) and/or improved clearance.

Some implementations may advantageously reduce the substituate amount which is infused together with the blood during the reinfusion.

In some implementations, blood continues to circulate in the extracorporeal circuit at least until $t_{BP\text{-}min}$ after ultrafiltration has stopped at $t_{UF\text{-}stop}$. In this way, in some cases, highly concentrated blood potentially present downstream of the blood filter may be replaced with fresh blood from the patient, which may have a lower hematocrit. This may allow for an ultrafiltration at blood return, which removes more fluid from the blood in the extracorporeal blood circuit than is achievable with more highly concentrated blood in the blood filter.

Thus, certain implementations may contribute to improving the effectiveness of the arterio-venous blood return, that is to say the simultaneous reinfusion both via the arterial and via the venous patient connection.

Since the method may be executed during a blood treatment session or directly after a blood treatment session has come to an end, it may be carried out easily and may not require any technically complex, time- and/or cost-intensive steps.

The method may preferably be carried out using standard substituate, which is already used in the blood treatment for other purposes, or with another liquid, which is already used in the blood treatment for other purposes, such as for example an isotonic saline solution, e.g., a 0.9% NaCl solution. This advantageously contributes to saving costs and time.

Further, the method may enable a removal of blood from the arterial section of the extracorporeal blood circuit and in particular from the arterial connection needle and the return of the blood into the vascular system of the patient. The step in reinfusion methods of the prior art by which the blood present in the arterial connection needle is pushed out in reverse flow, with the aid of, e.g., a syringe, which is filled with saline solution, may thus advantageously be avoided.

The method may thus offer the advantage of essentially completely recovering the blood present in the conduit interior of an extracorporeal blood circuit after its use for a blood treatment for the patient.

The method may ensure that no air enters the vascular system of the patient during emptying. Furthermore, in some implementations of the method no foaming in the area of a blood filter present in the extracorporeal blood circuit can occur, which would impede emptying the blood from the extracorporeal blood circuit. This may be advantageous as blood remaining in the blood filter or in the extracorporeal blood circuit constitutes a contamination risk.

DESCRIPTION OF DRAWINGS

Hereafter, the method is explained based on preferred implementations thereof with reference to the accompanying drawings.

DETAILED DESCRIPTION

During or after a blood treatment session, the blood or blood mixture in the extracorporeal blood circuit (and in particular in the blood filter) is typically returned to the patient. This usually takes place by introducing substituate into the extracorporeal blood circuit, whereby the blood present therein is displaced downstream and, thus, is re-infused into the patient, e.g. through the venous patient connection.

In some cases, due to the introduction of substituate, a diffuse transition region from blood to substituate develops, in which blood is mixed with substituate. The blood/substituate mixture present downstream of the blood filter (post-filter), thus, often contains substituate. A large amount of substituate may be needed to rinse out the extracorporeal blood circuit all the way to the venous patient connection. Additionally, some of this substituate is reintroduced to the patient, which is often undesired, particularly in dialysis patients.

Figure 1:
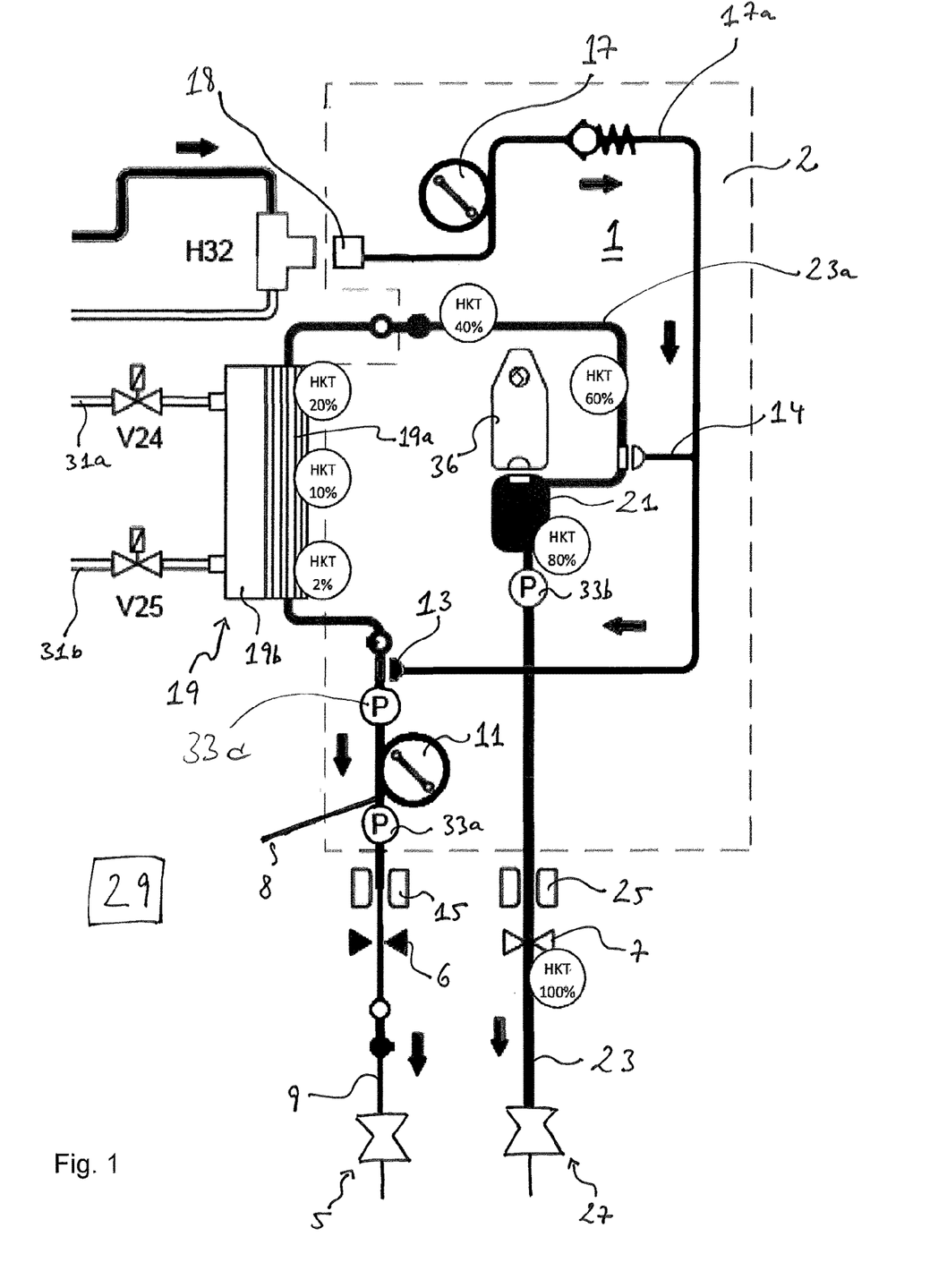
FIG. 1 shows, schematically simplified, the execution of a method from the prior art by means of a known medical treatment apparatus.
Figure 2:
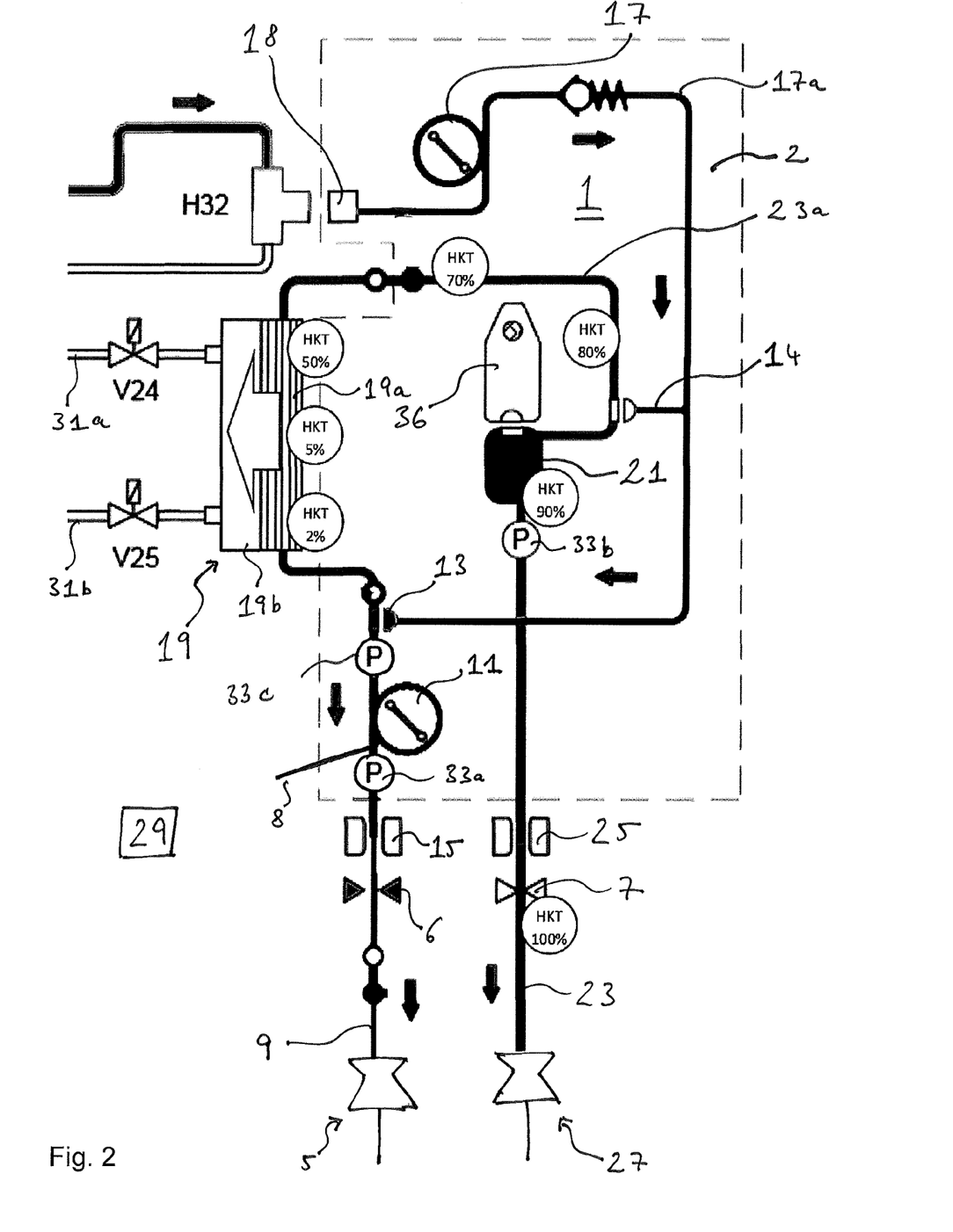
FIG. 2 shows, schematically simplified, an exemplary implementation of a medical treatment apparatus while executing the method.

Methods for removing blood from an extracorporeal blood circuit are shown in FIGS. 1 and 2. A conventional method is shown in FIG. 1. FIG. 2 shows an implementation of the method for removing blood and/or a blood mixture, which occurs in some implementations after a blood treatment session. Alternatively, it may occur during a blood treatment session. Both FIGS. 1 and 2 show schematically simultaneous reinfusion (also referred to as online closed circuit) and residual blood distribution at a time point at which half of the conventional reinfusion volume (e.g., about 200 ml) has been reinjected.

FIG. 1 shows an extracorporeal blood circuit 1, which is connected or connectable via a double needle access to the vascular system of the patient (not shown). The blood circuit 1 is disposed optionally in sections thereof in or on a blood cassette 2. It is connected to a blood treatment apparatus 4. Controlling or regulating the blood treatment apparatus 4 may be carried out by a control or regulating unit 29.

The extracorporeal blood circuit 1 includes an arterial patient tube 6 and an arterial connection needle 5 (as an example of an access device) of an arterial section 9 or of an arterial patient line or blood line 9. The extracorporeal blood circuit 1 further includes a venous patient tube clamp 7 and a connection needle 27 (as an example of a further or second access device) of a venous section 23 or of a venous patient line or blood line 23.

A blood pump 11 is provided in the arterial section 9, a substituate pump 17 is connected to a substituate line 17a. The substituate line 17a may be connected to a substituate source via an optional, preferably automatic substituate port 18, herein shown as not connected. By means of the substituate pump 17, substituate may be introduced via pre-dilution or via post-dilution through associated lines 13 or 14, respectively, into line sections, e.g., into the arterial section 9 or into a venous section 23a, respectively (between the blood chamber 19a and an optional single needle chamber 36) of the extracorporeal blood circuit 1.

A blood filter 19 is provided in the blood circuit 1. It includes the blood chamber 19a which is connected to the arterial section 9 and to the venous section 23. A dialysate chamber 19b of the blood filter 19 is connected to a fresh dialysis liquid inlet line 31a which leads to the dialysate chamber 19b and to a spent dialysate outlet line 31b which leads away from the dialysate chamber 19b.

The fresh dialysis liquid inlet line 31a optionally includes a valve V24 by means of which the flow within the fresh dialysis liquid inlet line 31a may be stopped. The spent dialysate outlet line 31b optionally includes a valve V25 by means of which the flow within the spent dialysate outlet line 31b may be stopped.

The fresh dialysis liquid inlet line 31a is further optionally connected to a compressed air source 26 (not shown here, see however FIG. 3) by means of another internal valve of the device. The compressed air source 26 may be provided as a part or component of the treatment apparatus 4 or may be a separate part therefrom. A pressure sensor 37 (herein not shown, see however FIG. 3) may be provided downstream of the compressed air source 26.

The arrangement of FIG. 1 encompasses an optional arterial detector 15 for detecting air and/or blood. The arrangement of FIG. 1 further encompasses one, two or more pressure sensor(s) 33a, 33b, 33c, e.g. at the points shown in FIGS. 1 and 2.

In order to empty the blood chamber 19a of the blood filter 19 from blood after the treatment, substitute may be added in pre-dilution to the blood circuit 1 and to the blood chamber 19a, as shown in FIG. 1, by the substitute pump 17 through the addition site 13.

Alternatively, or in addition, the substitute may be introduced without operating or not by exclusive operation of the substitute pump 17, but rather by (exclusively or additionally) operating the blood pump 11. To this end, e.g. the arterial patient hose clamp 6 is closed and substitute is introduced into the extracorporeal blood circuit 1 via a supply line 8 from a storage container for the substitute.

The substitute/blood content, thus produced, is conveyed along the conduit interior of the extracorporeal blood circuit 1 by operating the blood pump 11 and/or the substitute pump 17. The substitute/blood content is pressed or conveyed through the blood filter 19, a venous air separation chamber 21 and the venous section 23 of the extracorporeal blood circuit 1 in order to remove the blood from the extracorporeal blood circuit 1 in the direction towards the venous connection needle 27, from the blood filter 19.

A venous substitute-blood detector 25 is optionally arranged in the venous section 23 of the extracorporeal blood circuit 1 as an example of a detection device, which detects the presence of substitute at a pre-determined position of the conduit interior of the extracorporeal blood circuit 1. The blood pump 11 and/or the substitute pump 17 optionally continues conveying the substitute/blood content until the blood, which was present in the venous section 23 of the extracorporeal blood circuit 1, is removed from it and returned to the vascular system of the patient via the venous connection needle 27 and/or until the presence of substitute (or the decrease of the hematocrit in the conduit interior, for example down to 2%) is detected in the conduit interior at the venous substitute/blood detector 25. The conveying operation of all pumps may be stopped at this point. An optical and/or acoustical signal may be output.

FIG. 1 shows a distribution of residual blood after conveying half of the amount of the reinfusion fluid, which is conventionally required for removing blood from the blood tubing set 1. The hematocrit HKT at the venous substitute/blood detector 25 amounts to, at the point in time represented in FIG. 1, 100% of the original HKT value present in the extracorporeal blood circuit 1 immediately before the completion of the blood treatment method. The hematocrit HKT at the venous substitute/blood detector 25 is thus the original HKT value in the extracorporeal blood circuit 1 immediately before the completion of the blood treatment method. Therefore the hematocrit HKT is given in FIG. 1 as "HKT 100%" at the venous substitute/blood detector 25. All of the percentage values concerning HKT in FIG. 1 and in FIG. 2 are relative values: The percentage values given at the indicated points of the blood tubing circuit 1 indicate which fraction the HKT measurable at those points represents relative to the HKT present in the conduit interior at the end of the treatment, which is in this case when the ultrafiltration pump stops.

The hematocrit HKT of the blood present in the extracorporeal blood circuit 1 is described with HKT and a percentage value at the various points in FIG. 1. The percentage describes the relation of the current hematocrit HKT at the indicated points to the original hematocrit present in the extracorporeal blood circuit 1 immediately before completion of the blood treatment method. If for example the hematocrit HKT in the extracorporeal blood circuit 1 is 42% before the completion of the blood treatment, then "HKT 100%" means that the hematocrit HKT is still at 42%.

By infusing substitute using the substitute pump 17 through the addition site 13 for pre-dilution, a mixture in the extracorporeal blood circuit 1 occurs or develops at the transition from substitute to blood, in particular in the blood filter 19, which mixture influences the measurable HKT.

In FIG. 1, the hematocrit HKT at the entry of the blood chamber 19a of the blood filter 19 is 2% of the original value. The hematocrit HKT increases across the blood chamber 19a—initially to 10% and then at the venous end of the blood chamber 19a to 20% of the original measurable value. In the venous section 23, the hematocrit HKT further increases first to first 40% shortly after the blood filter 19, then to 60% in section 23a, to 80% after the air separation chamber 21 up to 100% at the venous substitute/blood detector 25 (in both FIG. 1 and FIG. 2. the indicated percentages refer to the ratio of the currently present hematocrit HKT to the original hematocrit HKT, see supra, and are thus relative values). It is now clear that in the prior art the mixing of substitute and blood takes place over a longer distance, such that a substantial volume of substitute must be infused for achieving a complete or an almost complete reinfusion of blood.

The method illustrated in a snapshot in FIG. 2—just as in FIG. 1—shows a residual blood distribution after conveying half of the fluid, which is conventionally reinfused. Unlike FIG. 1, there is a pressure difference in the blood filter 19 with a lower pressure in the dialysate chamber 19b and a higher pressure in the blood chamber 19a. The pressure difference may be e.g. created by generating an absolute or a relative negative pressure in the dialysate chamber 19b of the blood filter 19, e.g. by removing liquid from the dialysate chamber 19b through the valve V25 by means of an ultrafiltration pump (UF-pump 40, not shown, see FIG. 3). The pressure difference may be generated alternatively or additionally through a flow resistance downstream of the blood chamber 19a, e.g. in the venous section 23a, if at the same time fresh dialysis liquid is introduced into the blood chamber 19a, e.g. by means of the substitute pump 17 and/or the blood pump 11 or by another pump not shown in this implementation.

By means of the pressure difference, the liquid is removed from the extracorporeal blood circuit 1 (see arrow in the blood filter 19). This means that during the blood return, the hematocrit HKT in the extracorporeal blood circuit 1 is generally or at some times higher than in FIG. 1. This is seen at the blood filter 19, at the entry of which, just like in FIG. 1, a hematocrit HKT of 2% (of the original value) may be observed. At the exit of the filter 19, the hematocrit HKT is already 50% compared to 20% (of the original value, respectively) in the method shown in FIG. 1. This is due to the fact that water has been removed from the blood/substitute mixture in the blood filter 19.

At the points in FIG. 1, at which the hematocrit HKT is 40%, 60% and 80%, it is 70%, 80% or 90% in FIG. 2. The transition from blood to substitute is thus sharper than in the conventional method of FIG. 1. Less substitute is required for flushing out the blood/substitute mixture all the way to the venous patient connection. Furthermore, the blood/substitute mixture downstream of the filter 19 contains less substitute.

Figure 3:
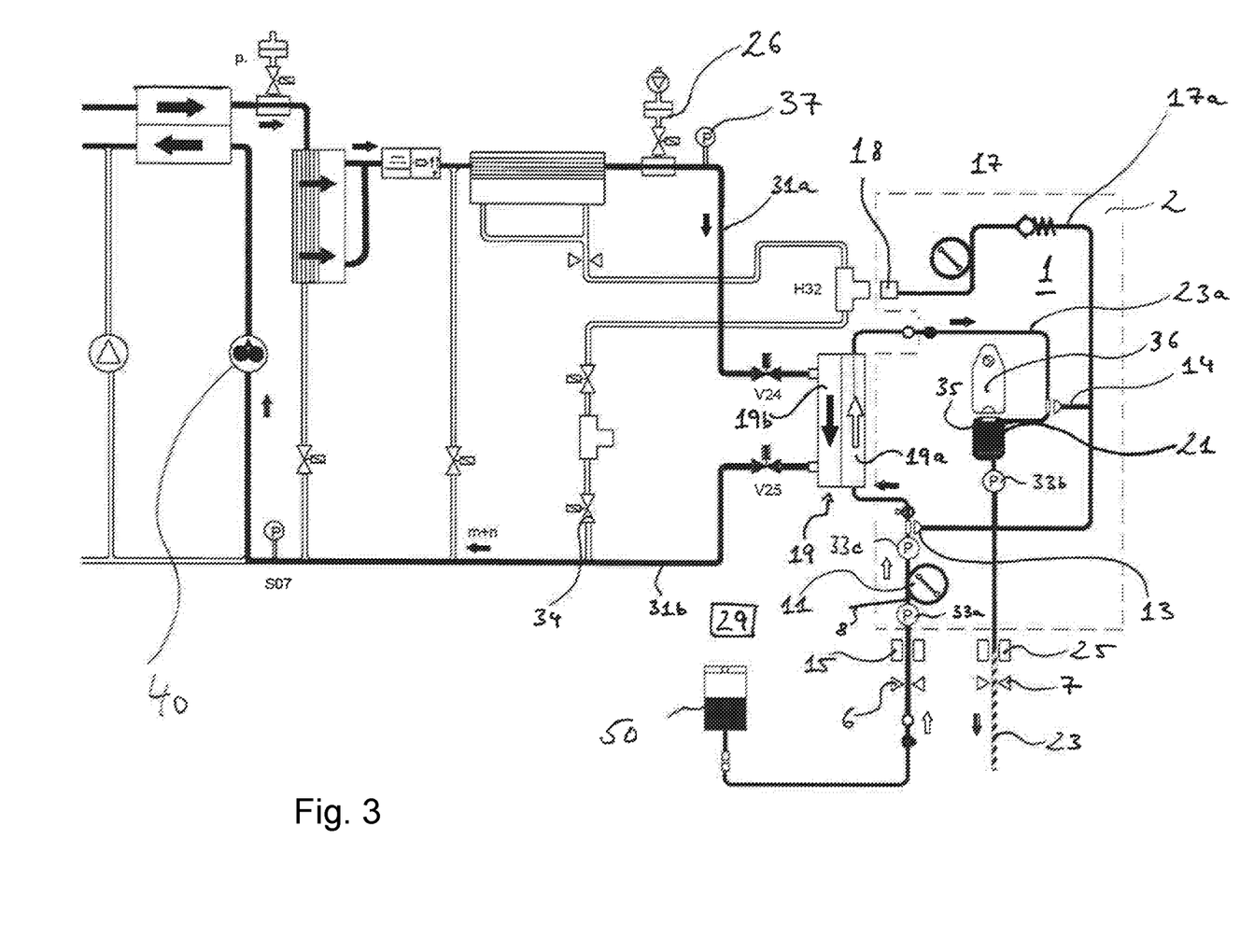
FIG. 3 shows a further method from the prior art, executed by a known medical treatment apparatus.

FIG. 3 shows an exemplary device behavior during a blood return known in the art. A bag 50 containing physiological saline which is placed at the arterial section 9 is a source for substitute with which the blood is displaced from the extracorporeal blood circuit 1. Unlike in FIGS. 1 and 2, the substitute is conveyed into the blood filter 19 with the aid of a blood pump 11.

In this implementation, no patient blood is cleaned in the blood filter 19 anymore, the dialysate chamber 19*b* and the membrane of the blood filter 19 are not perfused anymore so that the amount of water (plasma) in the patient blood is not reduced any further. Hence, the flow rate of the blood pump 11 reaches the patient (the flow rate is e.g. 30 to 200 ml/min). The valves V24 and V25 are both closed, and the UF pump 40 is switched off.

The arterial blood pump 11 conveys NaCl solution into the extracorporeal blood circuit 1. In this, the flow rate is e.g. 30 to 200 ml/min.

The device behavior during the blood return in an exemplary implementation may also be illustrated with reference to FIG. 3. The dialysate chamber 19*b* is optionally not perfused anymore in an implementation, i.e., there is no flow—except through the membrane—into the dialysate chamber. The amount of water (the plasma fraction) of the patient blood is further reduced. In this, the valve V24 is closed and the valve V25 is open. The UF pump 40 is switched on and pumps at e.g. 1 to 80 ml/min to generate a negative pressure in the dialysate chamber 19*b* and thereby removes water from the blood chamber 19*a* across the membrane. The arterial blood pump 11 here conveys for example NaCl solution from the bag at the arterial section 9 into the extracorporeal blood circuit 1 at a flow rate of e.g. 30 to 280 ml/min.

The flow rate within the extracorporeal blood circuit 1 across the membrane of the filter 19 to the treatment apparatus 4 is in this example equal to the conveying rate of the UF pump 40. The flow rate which reaches the patient is in this example the flow rate conveyed by the arterial pump minus the flow rate conveyed by the UF pump. The flow rate into the vascular system of the patient (the sum of arterial and venous flow rates) is here e.g. 30 to 200 ml/min.

Figure 4:
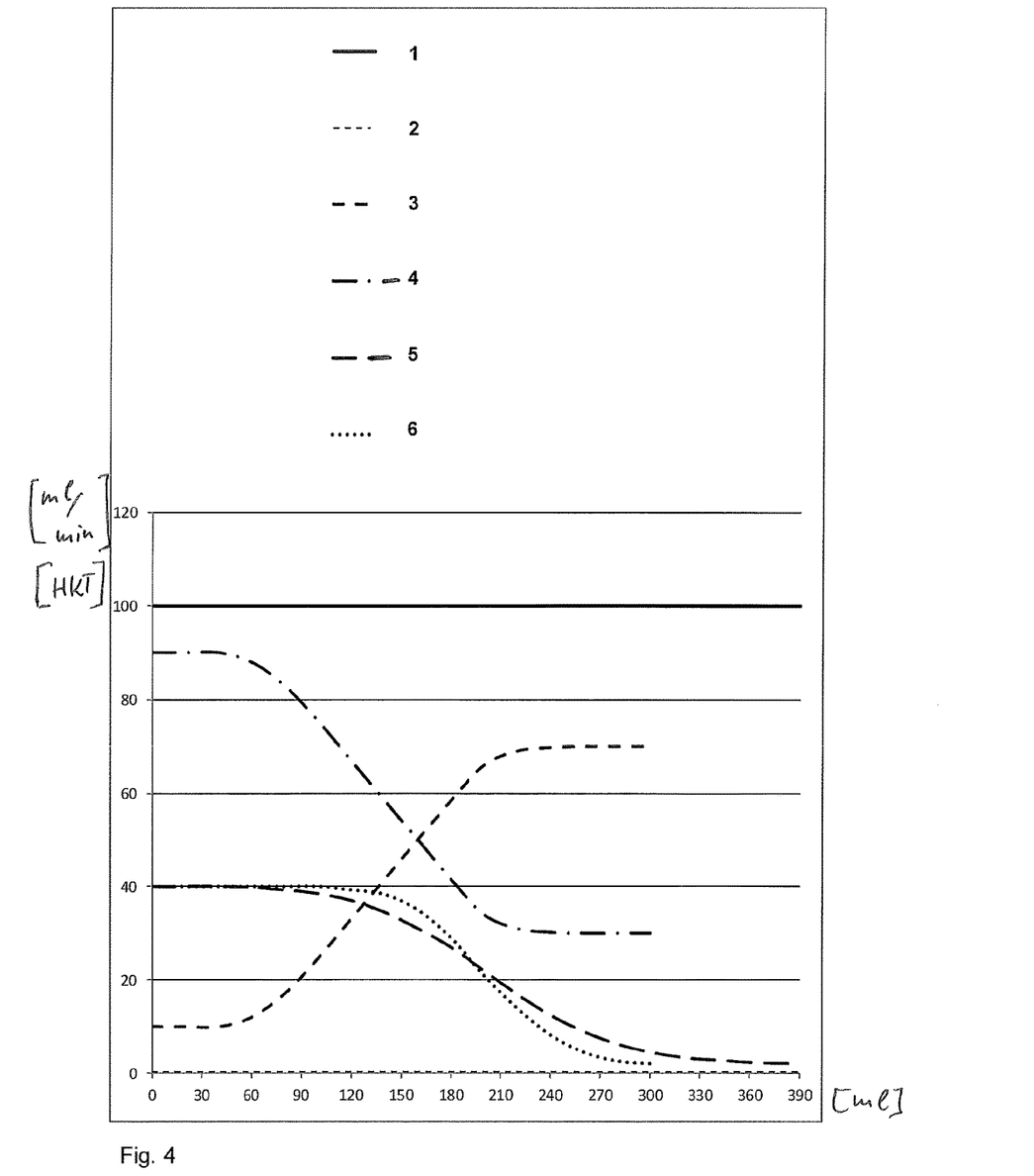
FIG. 4 shows the comparison between a traditional blood return with NaCl and a blood return by an implementation of the method.

FIG. 4 shows a comparison between a blood return in the prior art and an exemplary implementation of the method.

In this example, the method, advantageously reduces the required amount of substitute from the usual 390 ml to only 300 ml.

The continuous line (line 1) describes the flow rate present at the entry of the blood filter 19. This flow rate is optionally unchanged during the entire blood return in both the prior art and in the exemplary implementation of the method and may be 100 ml/min.

In the prior art, the conveying rate of the UF pump during the blood return is 0 ml/min, as seen in the thin, short dashed line (line 2). There is no flow across the filter membrane. Therefore, the flow rate at the entry of the blood filter 19 (line 1) is the same here as the flow rate at the exit of the filter 19.

In the prior art, this results in an absolute hematocrit HKT at the venous patient connection (line 5, long-dashed line), in this case at the venous substituate/blood detector 25, which is 40% at the beginning of the blood return. Due to the desired displacement of the blood by the substituate, the hematocrit HKT decreases at the detector 25 during the blood return until the hematocrit reaches a pre-determined value of e.g. 2% there. In the prior art, 390 ml physiological saline solution must be introduced into the extracorporeal blood circuit in order to reach this value of 2% (see x-axis of the diagram of FIG. 4).

In the implementation of the method which is exemplarily illustrated in FIG. 4, the flow rate at the filter exit (line 4, dot-dashed) is lower than the flow rate at the filter entry (line 1), because the UF pump 40 removes water from the dialysate chamber 19*b*. The flow rate of the UF pump 40 is shown in the bold, short-dashed line (line 3). Here, it is clear that the flow rate of the UF pump 40 increases across or during the blood return (line 3) with the result that the flow rate decreases at the filter exit (line 4). Water is removed from the blood/substituate mixture in the blood filter 19 by the UF pump 40, which causes the hematocrit HKT at the venous patient connection 27 to decrease to the pre-determined value (e.g. 2%) earlier already, namely after infusing only 300 ml substituate (line 6, dashed). Thus, for an almost complete reinfusion of the blood volume contained in the extracorporeal blood circuit 1, less substituate is infused than in the prior art.

Figure 5:
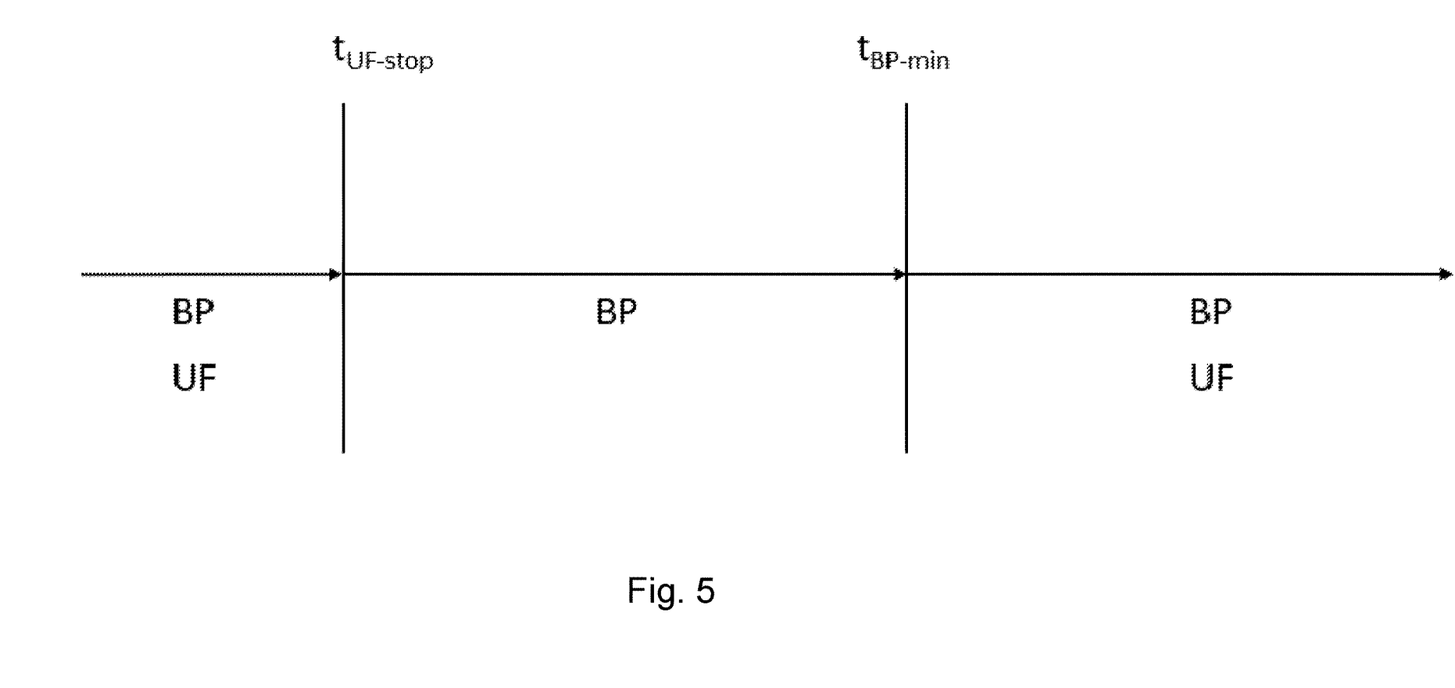
FIG. 5 illustrates the time period of blood pump operation in accord with aspects of the present disclosure.

In one example, blood is treated until an ultrafiltration goal is met and the ultrafiltration pump 40 is stopped at a time $t_{UF-stop}$ (FIG. 5). Subsequently, blood flow continues in the extracorporeal circuit 1, preferably without ultrafiltration taking place. To this end, the blood pump 11 is active while the ultrafiltration pump is preferably deactivated (preferably at least until $t_{BP-min}$). In this way, concentrated blood in the blood filter 19 is displaced by fresh blood from the patient. A blood measurement device, such as a blood volume monitor (e.g. CritLine), measures the hematocrit, alternatively a default value for the hematocrit is used (such a default value may be 35% and may be set by the clinician). The blood pump operates at least until $t_{BP-min}$ (FIG. 5), at which point in time at least a certain minimum volume $V_{post-UF-stop}$ has been conveyed by the blood pump since $t_{UF-stop}$, or a minimum time interval $T_{post-UF-stop}$ has elapsed since $t_{UF-stop}$ or a blood measurement, such as a hematocrit measurement value, falls below a certain threshold. Between $t_{UF-stop}$ and $t_{BP-min}$, the ultrafiltration pump is preferably deactivated.

After $t_{BP-min}$, the blood flow in the extracorporeal circuit 1 may be stopped and the arterial section 9 can be connected to a substituate supply, such as a bag of saline solution, or substituate may be provided by a substituate pump 17. Depending on the blood flow rate and the measured hematocrit value or default hematocrit value, the blood treatment apparatus 4 calculates a target ultrafiltration rate. In this, an ultrafiltration factor cf_UF is used as a safety parameter. The factor cf_UF describes the fraction of the water in the extracorporeal blood circuit 1, which may safely be removed from the extracorporeal blood circuit 1. In one implementation, cf_UF is 20%. This means that the water safely available in the extracorporeal blood circuit 1 is considered to be 20% of $V_{EBC}$. The target ultrafiltration rate $Q_{UF}$ is thus $Q_{UF}=Q_{BP} \times cf\_UF$ or $Q_{UF}=Q_{BP} \times 20\%$. Once blood return starts, for example by starting the blood pump 11, the ultrafiltration pump 40 will run at the target ultrafiltration rate. The ultrafiltration pump 40 runs until at least one of the following criteria is met, which takes into account the amount of blood in the blood filter 19:

(a) a pre-determined hematocrit is detected;
(b) the blood volume monitor (e.g. CritLine) measures a predefined saturation level;
(c) a user selectable relative blood volume;
(d) a default or user selectable preset substituate volume; and (e) a predefined post-arterial pump pressure, dialysate pressure, transmembrane or venous pressure is detected.

When the ultrafiltration pump 40 is stopped, the blood pump 11 continues running until blood is no longer sensed at the venous clamp or a set volume of substitute is processed. The described process may also be used in conjunction with priming solutions created online by a dialysis machine.

The present methods and devices are not limited to the above-described implementations, which are given for illustration only.

LIST OF REFERENCE NUMERALS 1 extracorporeal blood circuit
2 blood cassette
4 treatment apparatus, blood treatment apparatus
5 access device, e.g. arterial connection needle
6 arterial patient hose clamp
7 venous patient hose clamp
8 supply line
9 arterial section or arterial blood line or arterial patient line
11 blood pump
13 addition site for substitute (pre-dilution)
14 addition site for substitute (post-dilution)
15 arterial air/blood detector
17 second conveying device, e.g. a substitute pump
17a substitute line
18 automatic substitute port
19 blood filter, filter
19a blood chamber
19b dialysate chamber
21 venous air separator chamber
23 venous section or venous blood line
23a venous section
25 venous substitute/blood detector
26 compressed air source
27 access device, e.g. venous connection needle, venous patient connection
29 control or regulating unit
31a fresh dialysis liquid inlet line
31b spent dialysate outlet line
33a, b, c pressure sensors
35 single needle valve
36 single needle chamber
37 pressure sensor
40 ultrafiltration pump (UF pump)
V24 valve
V25 valve
50 bag
HKT hematocrit

What is claimed is:

1. A method for operating a blood treatment system, the method comprising:
    at the end of a blood treatment session, continuing to operate a blood pump from a first time point signifying (i) regular completion of the blood treatment session or (ii) manual termination of the blood treatment session by a user, at which an ultrafiltration pump is stopped, at least until a second time point, at which at least one of the following conditions is first met after the first time point:
    (a) a time interval has elapsed;
    (b) the blood pump has conveyed a volume after the first time point; and
    (c) a measurement value of a fluid in an extracorporeal blood circuit of the blood treatment system exceeds or falls below a certain threshold,
    wherein before the first time point, the ultrafiltration pump and the blood pump are running, and wherein at the first time point, the ultrafiltration pump stops running and the blood pump continues running.

2. The method according to claim 1, wherein the first time point occurs after at least one of:
    an ultrafiltration goal has been met; and
    a prescribed treatment time has been reached.

3. The method according to claim 1, wherein the method comprises operating the blood pump after the first time point at least until condition (c) of claim 1 has been met and at least until at least one of the conditions (a) and (b) of claim 1 is met.

4. The method according to claim 1, wherein after the second time point the ultrafiltration pump is reactivated.

5. The method according to claim 4, wherein a target rate of the ultrafiltration pump is calculated based on a flow rate, the measurement value of the fluid in the extracorporeal blood circuit and/or on water available in the extracorporeal blood circuit.

6. The method according to claim 1, wherein after the second time point, a fluid content of the extracorporeal blood circuit is returned to a patient by introducing a substituate into an arterial section of the extracorporeal blood circuit.

7. The method according to claim 6, wherein for at least some of a time period, during which the fluid content of the extracorporeal blood circuit is returned to the patient, at least one of the following is operated:
    the ultrafiltration pump;
    the blood pump; and
    a substituate pump.

8. The method according to claim 7, wherein during return of the fluid content of the extracorporeal blood circuit to the patient, the ultrafiltration pump is operated, after the ultrafiltration pump was stopped at the first time point and was reactivated no earlier than the second time point, at least until at least one of the following conditions is met:
    (d) the measurement value of the fluid in the extracorporeal blood circuit of the blood treatment system exceeds or falls below a certain threshold;
    (e) a rinsing fluid volume introduced into the arterial section exceeds a certain value; and
    (f) a detected pressure exceeds a certain value.

9. The method according to claim 8, wherein the substituate is introduced into the arterial section by the blood pump and wherein after the ultrafiltration pump has stopped due to at least one of the conditions (d), (e) and (f) of claim 8 being met, the blood pump continues running until at least one of the following conditions is met:
    (g) a measurement value recorded in a venous section of the extracorporeal blood circuit exceeds or falls below a certain threshold; and
    (h) the rinsing fluid volume introduced into the arterial section exceeds a certain value.

10. The method according to claim 7, wherein a pressure difference is generated in a blood filter of the extracorporeal blood circuit with a lower pressure in a dialysate chamber and a higher pressure in a blood chamber of the extracorporeal blood circuit, wherein the pressure difference is, at least partially, generated by at least one pump of the following pumps:
    the ultrafiltration pump;
    the substituate pump; and
    the blood pump.

11. The method according to claim 10, wherein a flow rate of the at least one pump is between 30 and 280 ml/min.

12. The method according to claim 10, wherein at least one of the following ratios is in a value range of 0.01 to 0.8:
- a first flow rate ratio of the ultrafiltration pump to the blood pump; and
- a second flow rate ratio of the ultrafiltration pump to the substituate pump.

13. The method according to claim 6, wherein a first flow rate ratio of the ultrafiltration pump to the blood pump and/or a second flow rate ratio of the ultrafiltration pump to a substituate pump increases while substituate is introduced into the arterial section.

14. The method according to claim 6, wherein a first flow rate ratio of the ultrafiltration pump to the blood pump and/or a second flow rate ratio of the ultrafiltration pump to a substituate pump is varied while substituate is introduced into the arterial section of the extracorporeal blood circuit in order to regulate hematocrit in a venous section of the extracorporeal blood circuit to a pre-determined value.

15. The method according to claim 1, wherein the extracorporeal blood circuit comprises a blood filter having a blood chamber and a dialysate chamber between which a membrane is arranged, wherein the blood chamber is connected to an arterial section which leads to the blood chamber, and to a venous section which leads away from the blood chamber, and wherein the dialysate chamber is connected to a dialysis inlet line which leads to the dialysate chamber and to a dialysate outlet line which leads away from the dialysate chamber.

16. A medical treatment apparatus comprising:
an extracorporeal blood circuit with a conduit interior;
a blood pump which is arranged at or in the extracorporeal blood circuit for conveying blood within the conduit interior of the extracorporeal blood circuit; and
a control unit configured to:
at the end of a blood treatment session, continuing to operate the blood pump from a first time point signifying (i) regular completion of the blood treatment session or (ii) manual termination of the blood treatment session by a user, at which an ultrafiltration pump is stopped, at least until a second time point, at which at least one of the following conditions is first met after the first time point:
(a) a time interval has elapsed;
(b) the blood pump has conveyed a volume after the first time point; and
(c) a measurement value of a fluid in the extracorporeal blood circuit exceeds or falls below a certain threshold,
wherein before the first time point, the ultrafiltration pump and the blood pump are running, and wherein at the first time point, the ultrafiltration pump stops running and the blood pump continues running.

17. The medical treatment apparatus according to claim 16, which comprises or is connected to at least one pump for generating a pressure difference in a blood filter of the extracorporeal blood circuit, with a lower pressure in a dialysate chamber and a higher pressure in a blood chamber of the extracorporeal blood circuit.

18. A non-transitory computer readable medium storing instructions that are executable by one or more processors configured to perform operations comprising:
at the end of a blood treatment session, continuing to operate a blood pump from a first time point signifying (i) regular completion of the blood treatment session or (ii) manual termination of the blood treatment session by a user, at which an ultrafiltration pump is stopped, at least until a second time point, at which at least one of the following conditions is first met after the first time point:
(a) a time interval has elapsed;
(b) the blood pump has conveyed a volume after the first time point; and
(c) a measurement value of a fluid in an extracorporeal blood circuit exceeds or falls below a certain threshold,
wherein before the first time point, the ultrafiltration pump and the blood pump are running, and wherein at the first time point, the ultrafiltration pump stops running and the blood pump continues running.

\* \* \* \* \*